United States Patent
Laikhter et al.

(10) Patent No.: US 9,540,515 B2
(45) Date of Patent: *Jan. 10, 2017

(54) FLUORESCENCE QUENCHING AZO DYES, THEIR METHODS OF PREPARATION AND USE

(71) Applicant: Integrated DNA Technologies, Inc., Skokie, IL (US)

(72) Inventors: Andrei Laikhter, Lexington, MA (US); Mark Aaron Behlke, Coralville, IA (US); Joseph Walder, Chicago, IL (US); Kevin William Roberts, Iowa City, IA (US); Yawfui Yong, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 192 days.

This patent is subject to a terminal disclaimer.

(21) Appl. No.: 13/736,999

(22) Filed: Jan. 9, 2013

(65) Prior Publication Data

US 2013/0116415 A1    May 9, 2013

Related U.S. Application Data

(60) Continuation of application No. 13/298,479, filed on Nov. 17, 2011, now Pat. No. 8,377,641, which is a division of application No. 12/252,721, filed on Oct. 16, 2008, now Pat. No. 8,084,588, which is a division of application No. 10/987,608, filed on Nov. 12, 2004, now Pat. No. 7,439,341.

(60) Provisional application No. 60/520,077, filed on Nov. 14, 2003.

(51) Int. Cl.

| | | |
|---|---|---|
| C09B 39/00 | (2006.01) | |
| C09B 29/00 | (2006.01) | |
| C07C 245/10 | (2006.01) | |
| C07F 9/09 | (2006.01) | |
| C07F 9/24 | (2006.01) | |
| C07H 21/04 | (2006.01) | |

(52) U.S. Cl.
CPC ............ *C09B 29/00* (2013.01); *C07C 245/10* (2013.01); *C07F 9/091* (2013.01); *C07F 9/2408* (2013.01); *C07H 21/04* (2013.01); *Y10T 436/143333* (2015.01)

(58) Field of Classification Search
CPC ..................................................... C09B 39/00
USPC ........................................................ 534/727
See application file for complete search history.

(56) References Cited

U.S. PATENT DOCUMENTS

| | | |
|---|---|---|
| 2,264,303 A | 12/1941 | Dickey |
| 3,218,309 A | 11/1965 | Elslager et al. |
| 3,407,189 A | 10/1968 | Merian |
| 3,970,617 A | 7/1976 | Bruno |
| 4,358,535 A | 11/1982 | Falkow et al. |
| 4,439,356 A | 3/1984 | Khanna et al. |
| 4,683,194 A | 7/1987 | Saiki et al. |
| 4,683,195 A | 7/1987 | Mullis et al. |
| 4,683,202 A | 7/1987 | Mullis |
| 4,711,955 A | 12/1987 | Ward et al. |
| 4,820,630 A | 4/1989 | Taub |
| 4,868,103 A | 9/1989 | Stavrianopoulos et al. |
| 4,868,105 A | 9/1989 | Urdea et al. |
| 4,889,818 A | 12/1989 | Gelfand et al. |
| 4,914,210 A | 4/1990 | Levenson et al. |
| 4,954,630 A | 9/1990 | Klein et al. |
| 4,996,143 A | 2/1991 | Heller et al. |
| 5,011,769 A | 4/1991 | Duck et al. |
| 5,108,892 A | 4/1992 | Burke et al. |
| 5,124,246 A | 6/1992 | Urdea et al. |
| 5,188,934 A | 2/1993 | Menchen et al. |
| 5,210,015 A | 5/1993 | Gelfand et al. |
| 5,214,136 A | 5/1993 | Lin et al. |
| 5,272,259 A | 12/1993 | Claussen et al. |
| 5,304,645 A | 4/1994 | Klein et al. |
| 5,312,728 A | 5/1994 | Lizardi et al. |

(Continued)

FOREIGN PATENT DOCUMENTS

| | | |
|---|---|---|
| DE | 2546535 | 4/1977 |
| EP | 0070685 | 1/1983 |

(Continued)

OTHER PUBLICATIONS

US 6,255,052, 05/2001, Batz et al. (withdrawn)

(Continued)

*Primary Examiner* — Yong Chu
*Assistant Examiner* — Sonya Wright
(74) *Attorney, Agent, or Firm* — Michael Best & Friedrich LLP

(57) ABSTRACT

Disclosed is a group of azo quencher compositions useful as fluorescence quenchers having the general structure of formula 1, methods of making or using the compositions, and kits comprising the composition.

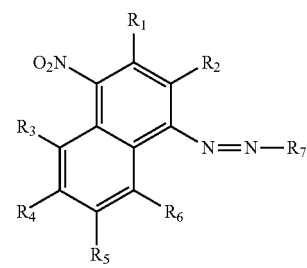

Formula 1

9 Claims, 1 Drawing Sheet

(56) References Cited

U.S. PATENT DOCUMENTS

| | | |
|---|---|---|
| 5,326,679 A | 7/1994 | Yanagisawa et al. |
| 5,328,824 A | 7/1994 | Ward et al. |
| 5,451,463 A | 9/1995 | Nelson et al. |
| 5,455,157 A | 10/1995 | Hinzpeter et al. |
| 5,487,972 A | 1/1996 | Gelfand et al. |
| 5,492,806 A | 2/1996 | Drmanac et al. |
| 5,502,177 A | 3/1996 | Matteucci et al. |
| 5,512,667 A | 4/1996 | Reed et al. |
| 5,514,785 A | 5/1996 | Van Ness et al. |
| 5,525,464 A | 6/1996 | Drmanac et al. |
| 5,556,752 A | 9/1996 | Lockhart et al. |
| 5,696,251 A | 12/1997 | Arnold, Jr. et al. |
| 5,801,155 A | 9/1998 | Kutyavin et al. |
| 5,804,375 A | 9/1998 | Gelfand et al. |
| 5,824,796 A | 10/1998 | Petrie et al. |
| 5,830,653 A | 11/1998 | Froehler et al. |
| 5,846,726 A | 12/1998 | Nadeau et al. |
| 5,849,482 A | 12/1998 | Meyer, Jr. et al. |
| 5,876,930 A | 3/1999 | Livak et al. |
| 5,942,610 A | 8/1999 | Nelson et al. |
| 5,952,202 A | 9/1999 | Aoyagi et al. |
| 6,007,992 A | 12/1999 | Lin et al. |
| 6,028,183 A | 2/2000 | Lin et al. |
| 6,114,518 A | 9/2000 | Pitner et al. |
| 6,117,973 A | 9/2000 | Batz et al. |
| 6,117,986 A | 9/2000 | Nardone et al. |
| 6,214,979 B1 | 4/2001 | Gelfand et al. |
| 6,312,894 B1 | 11/2001 | Hedgpeth et al. |
| 6,316,610 B2 | 11/2001 | Lee et al. |
| 6,323,337 B1 | 11/2001 | Singer et al. |
| 6,399,392 B1 | 6/2002 | Haugland et al. |
| 6,416,953 B1 | 7/2002 | Heller |
| 6,441,159 B1 | 8/2002 | Lukhtanov et al. |
| 6,448,407 B1 | 9/2002 | Lee et al. |
| 6,451,535 B1 | 9/2002 | Jenne et al. |
| 6,465,175 B2 | 10/2002 | Horn et al. |
| 6,465,644 B1 | 10/2002 | Yan et al. |
| 6,485,901 B1 | 11/2002 | Gildea et al. |
| 6,531,581 B1 | 3/2003 | Nardone et al. |
| 6,531,589 B1 | 3/2003 | Iyer et al. |
| 6,531,591 B1 | 3/2003 | Fensholdt |
| 6,576,752 B1 | 6/2003 | Manoharan et al. |
| 6,653,473 B2 | 11/2003 | Reed et al. |
| 6,699,975 B2 | 3/2004 | Reed et al. |
| 6,727,356 B1 | 4/2004 | Reed et al. |
| 6,790,945 B2 | 9/2004 | Lukhtanov et al. |
| 6,800,728 B2 | 10/2004 | Schwartz |
| 6,825,331 B2 | 11/2004 | Manoharan et al. |
| 6,875,858 B1 | 4/2005 | DeFrancq et al. |
| 7,122,383 B2 | 10/2006 | Jones et al. |
| 7,173,125 B2 | 2/2007 | Schwartz et al. |
| 7,439,341 B2 | 10/2008 | Laikhter et al. |
| 7,476,735 B2 | 1/2009 | Laikhter et al. |
| 7,605,243 B2 | 10/2009 | Laikhter et al. |
| 7,645,872 B2 | 1/2010 | Laikhter et al. |
| 7,803,536 B2 | 9/2010 | Laikhter et al. |
| 7,803,936 B2 | 9/2010 | Laikhter et al. |
| 8,030,460 B2 | 10/2011 | Laikhter et al. |
| 8,084,588 B2 | 12/2011 | Laikhter et al. |
| 8,114,979 B2 | 2/2012 | Laikhter et al. |
| 8,377,641 B2 * | 2/2013 | Laikhter et al. ............ 435/6.11 |
| 2002/0034754 A1 | 3/2002 | Reed et al. |
| 2002/0137070 A1 | 9/2002 | Elghanian et al. |
| 2003/0082547 A1 | 5/2003 | Ewing et al. |
| 2003/0096254 A1 | 5/2003 | Reed et al. |
| 2003/0144499 A1 | 7/2003 | McGall et al. |
| 2004/0110308 A1 | 6/2004 | Laikhter et al. |
| 2004/0180343 A1 | 9/2004 | Weber |
| 2005/0112673 A1 | 5/2005 | Laikhter et al. |
| 2006/0263816 A1 | 11/2006 | Laikhter et al. |
| 2007/0218490 A1 | 9/2007 | Laikhter et al. |
| 2009/0053821 A1 | 2/2009 | Laikhter et al. |
| 2009/0118482 A1 | 5/2009 | Laikhter et al. |
| 2009/0299041 A1 | 12/2009 | Laikhter et al. |
| 2010/0076181 A1 | 3/2010 | Laikhter et al. |
| 2010/0298554 A1 | 11/2010 | Laikhter et al. |
| 2011/0060150 A1 | 3/2011 | Laikhter et al. |
| 2011/0236898 A1 | 9/2011 | Rose et al. |
| 2011/0319606 A1 | 12/2011 | Laikhter et al. |

FOREIGN PATENT DOCUMENTS

| | | |
|---|---|---|
| EP | 0070686 | 1/1983 |
| EP | 0070687 | 1/1983 |
| EP | 0152886 | 8/1985 |
| EP | 0185494 | 6/1986 |
| EP | 0246864 | 11/1987 |
| EP | 0272007 | 6/1988 |
| EP | 0320308 | 6/1989 |
| EP | 0357011 | 3/1990 |
| EP | 0439182 | 7/1991 |
| EP | 1907560 | 4/2008 |
| GB | 1394368 | 5/1975 |
| GB | 1533121 | 11/1978 |
| JP | 52-88681 | 7/1977 |
| JP | 52-91031 | 8/1977 |
| WO | WO 89/09284 | 10/1989 |
| WO | WO 89/10979 | 11/1989 |
| WO | WO 90/14353 | 11/1990 |
| WO | WO 91/05060 | 4/1991 |
| WO | WO 92/10588 | 6/1992 |
| WO | WO 96/17957 | 6/1996 |
| WO | WO 96/28460 | 9/1996 |
| WO | WO 96/34983 | 11/1996 |
| WO | WO 96/40662 | 12/1996 |
| WO | WO 97/29154 | 8/1997 |
| WO | WO 97/39008 | 10/1997 |
| WO | WO 99/14226 | 3/1999 |
| WO | WO 99/37717 | 7/1999 |
| WO | WO 99/40226 | 8/1999 |
| WO | WO 99/51621 | 10/1999 |
| WO | WO 99/51775 | 10/1999 |
| WO | WO 99/64431 | 12/1999 |
| WO | WO 00/06771 | 2/2000 |
| WO | WO 00/70685 | 11/2000 |
| WO | WO 01/04129 | 1/2001 |
| WO | WO 01/42505 | 6/2001 |
| WO | WO 01/86001 | 11/2001 |
| WO | WO 2004/026804 | 4/2004 |
| WO | WO 2004/113562 | 12/2004 |
| WO | WO 2005/049849 | 6/2005 |
| WO | 2006/081035 | 8/2006 |
| WO | WO 2006/127507 | 4/2007 |
| WO | 2010/147673 | 12/2010 |

OTHER PUBLICATIONS

STN/CAS online results Takai (1991).*
STN/CAS online results Gambarov (1982).*
STN/CAS online results Hugentobler (1982).*
STN/CAS online results Sakharova (1975).*
Ansanuma et al., "Enantioselective Incorporation of Azobenzenes into Oligodeoxyribonucleotide for Effective Photoregulation of Duplex Formation**", Angew. Chem. Int. Ed., vol. 40, No. 14, Jan. 1, 2001, pp. 2671-2673.
Liang et al., "An interstrand-wedged duplex composed of alternating DNA base pairs and covalently attached intercalators," Journal of Material Chemistry, vol. 20, No. 3, Jan. 1, 2009, p. 575.
Ossipov et al., "Dipyrido[3,2-a:2', 3'-c]phenazi ne-Tethered Oligo-DNA: Synthesis and Thermal Stability of Their DNA'DNA and DNA'RNA Duplexes and DNA'DNA'DNA Triplexes", Helvetica Chimica Acta, vol. 82, Jan. 1, 1999, pp. 2186-2200.
Prokhorenko et al., "Incorporation of a pyrene nucleoside analogue into synthetic oligodeoxynucleotides using a nucleoside-like synthon", Bioorganic & Medicinal Chemistry Letters, Pergamon, vol. 5, No. 18, Sep. 21, 1995, pp. 2081-2084.
Schnippering et al., "Synthesis and electrochemical properties of TTF modified oligodeoxynucleotides," Chemical Communications, No. 37, Jan. 1, 2009, p. 5552.
Shi et al., "Design of Phosphoramidite Monomer for Optimal Incorporation of Functional Intercalator to Main Chain of Oligo-

(56) References Cited

OTHER PUBLICATIONS nucleotide," Bioconjugate Chemistry, vol. 16, No. 2, Mar. 1, 2005, pp. 306-311.
7th International Symposium, held 2001, pp. 1-14, 7th International Symposium & Exhibition Solid Phase Synthesis & Combinatorial Chemical Libraries, Sep. 18-22, 2001—University of Southampton, England, UK.
Agrawal, S. et al., "Efficient methods for attaching non-radioactive labels to the 5' ends of synthetic oligodeoxyribonucleotides," Nuc. Acids Res. (1986) 14:6227-6245.
Austermann, S. et al., "Inhibition of human immunodeficiency virus type 1 reverse transcriptase by 3'-blocked oligonucleotide primers," Biochem. Pharm. (1992) 43(12):2581-2589.
Bollum, F.J., "Oligodeoxyribonucleotide-primed reactions catalyzed by calf thymus polymerase," J. Bio. Chem. (1962) 237(6):1945-1949.
Boturyn, D. et al., "Synthesis of Fluorescent probes for the Detection of Abasic Sites in DNA," Tetrahedron (1997) 53(15):5485-5492.
Cardullo, R.A et al., "Detection of nucleic acid hybridization by nonradiative fluorescence resonance energy transfer," Proc. Natl. Acad. Sci. USA (1988) 85:8790-8794.
Conference Proceedings, retrieved 2010, two pages, Innovation and Perspectives in Solid Phase Synthesis & Combinatorial Libraries: Peptides, Proteins and Nucleic Acids—Small Molecule Organic Chemistry Diversity, Collected Papers, International Symposium, 7th, Southampton, United Kingdom, Sep. 18-22, 2001, Roger Epton, Editor.
Dey, S. and Sheppard, T.L., "Ketone-DNA: a versatile postsynthetic DNA decoration platform," Org. Lett. (2001) 3(25):3983-3986.
Easy Q&Q PCR, http://www.eurogentec.be/code/en/product_easy_qq.htm, visited May 9, 2002, 4 pages.
Gelfand, D.H., "Taq DNA Polymerase," PCR Technology Principles and Applications for DNA Amplification, Stockton Press, NY, Ehrlich ed. (1989) Ch. 2, 17-22.
Genbank Accession No. AF298116, Rose et al., "Mus musculus bHLH protein Ptfl-p48 gene," (2001) 6 pages.
Gibson, V. et al., "Molecular modelling of anthraquinone-oligodeoxynucleotide conjugates," Pharm. Sci. (1996) 2:545-548.
Gorelick, M.V. et al., "Effect of benzannelation on the coloration of p-aminoazo compounds," Zhurnal Organicheskoi Khimii (1980) 16(9):1927-1933—Abstract only—Accession No. 1981:193676.
Greene, T.W. and Wuts, P.G.M., *Protective Groups in Organic Synthesis*, (1999) 3rd Ed. John Wiley & Sons, Inc., U.S.
Haugland, R.P. et al., *Handbook of Flourescent Probes and Research Chemicals*, (1992) 5th Ed. Molecular Probes, Inc., Oregon, U.S.
Heesemann, J., "Studies on monolayers. 1. Surface tension and absorption spectroscopic measurements of monolayers of surface-active azo and stilbene dyes," J. Am. Chem. Soc. (1980) 102(7):2167-2176.
Heller, M.J. et al., "Chemiluminescent and fluorescent probes for DNA hybridization systems," Rapid Detection and Identification of Infectious Agents (1985) Academic Press, Inc., Orlando, Kingsbury et al. eds. 245-256.
Ho, M.S. et al., "Azo polymers for reversible optical storage. 7. The effect of the size of the photochromic groups," Macromolecules (1995) 28(18):6124-6127 (Abstract only—Accession No. 1995:746851).
Hugentobler, M. et al., "Compounds with a metal-arene σ-bond. Part 2. Cyclometalation of arylazo compounds. Part 2. Regioselectivity of the cyclopalladation of some substituted 1-arylazonaphthalenes," Helvetica Chimica Acta (1982) 65(4):1202-1211 (Abstract only—Accession No. 1982:616430).
Ito, T. et al., "Reductive Electron Injection into Duplex DNA by Aromatic Amines," J. Am. Chem. Soc. (2004) 126: 15552-15559.
Iyer, R.P. et al., "3H-1,2-benzodithiole-3-one 1,1-dioxide as an improved sulfurizing reagent in the solid-phase synthesis of oligodeoxyribonucleoside phosphorothioates," J. Am. Chem. Soc. (1990) 112:1253-1254.

Jenkins, J.H., Senior Librarian at the United States Patent and Trademark Office, email dated Mar. 18, 2010 and previously related email corespondence, pp. 1-2.
Johansson, M.K. et al., "Time gating improves sensitivity in energy transfer assays with terblum chelate/dark quencher oligonucleotide probes," J. Am. Chem. Soc. (2004) 126:16451-16455.
Ju, J. et al., "Fluorescence energy transfer dye-labeled primers for DNA sequencing and analysis," Proc. Natl. Acad. Sci. USA (1995) 92:4347-4351.
Kerzhner, B.K. et al., "Photoisomerization of aromatic azo compounds adsorbed on a hydroxylated surface," Zhurnal Obshchei Khimii (1983) 53(10):2303-2306 (Abstract only—Accession No. 1984:50840).
Kuball, H-G. et al., "Helical twisting power of chiral mono- and bis-aminoanthraquinones," J. Mater. Chem. (1995) 5(12):2167-2174.
Lawyer, F.C. et al., "Isolation, characterization, and expression in *Escherichia coli* of the DNA polymerase gene from thermus aquaticus," J. Biol. Chem. (1989) 264(11):6427-6437.
Lehman, I.R. et al., "Persistence of deoxyribonucleic acid polymerase I and its 5' →3' exonuclease activity in PolA mutants of *Escherichia coli* K12," J. Biol. Chem. (1973) 248(22):7717-7723.
Marshall, "Rules for the visible absorption spectra of halogenated fluorescein dyes," Histochemical J. (1975) 7:299-303.
Matthews, J.A. et al., "Analytical strategies for the use of DNA probes," Analy. Biochem. (1988) 169:1-25.
May, J.P. et al., "A new dark quencher for use in genetic analysis," Chem. Commun. (2003) 970-971.
May, J.P. et al., "A novel dark quencher for oligonucleotide probes: synthesis and applications," poster presentation from TIDES 2002 IBC Oligonucleotide and Peptide Technology Conference, May 6-8, 2002, Las Vegas, Nevada (2 pages).
May, J.P. et al., "Synthesis of a novel dark quencher for use with long wavelength dyes in oligonucleotide probes," Innovation and Perspectives in Solid Phase Synthesis & Combinatorial Libraries: Peptides, Proteins and Nucleic Acids Small Molecule Organic Chemical Diversity, Collected Papers, 7th International Symposium, Southampton, United Kingdom, Sep. 18-22, 2002, 231-233.
Misiura, K. et al., "Biotinyl and phosphotyrosinyl phosphoramidite derivatives useful in the incorporation of multiple reporter groups on synthetic oligonucleotides," Nucleic Acids Research (1990) 18(15):4345-4354.
Miyashita, T. et al., "Novel dinucleoside phosphotriester unit conjugated with an intercalative moiety in a stereospecific manner enhances thermal stability of an alternate-stranded triple helix," Tetrahedron Letters (2003) 44:7399-7402.
Mori, K. et al., "Oligodeoxynucleotide analogs with 5'-linked anthraquinone," FEBS Letters (1989) 249(2):213-218.
Morier-Teissier, E. et al., "Free radical production and DNA cleavage by copper chelating peptide-anthraquinones," Anti-Cancer Drug Design (1990) 5:291-305.
Morrison, L.E. et al., "Solution-phase detection of polynucleotides using interacting fluorescent labels and competitive hybridization," Anal. Biochem. (1989) 183:231-244.
Mullis, K. et al., "Specific Enzymatic Amplification of DNA in Vitro: The Polymerase Chain Reaction," Cold Spring Harbor Symp. Quant. Biol. (1986) 51:263-273.
Noble, S.A. et al, "Methylphosphonates as probes of protein-nucleic acid interactions," Nuc. Acids Res. (1984) 12(7):3387-3404.
PR Newswire, Announcing IBC's TIDES 2002: Oligonucleotide and Peptide Technology Conferences May 6-8, 2002, Las Vegas, NV, Copyright 2002, PR Newswire Association LLC, pp. 1-2, website (retrieved Mar. 18, 2010): http://www.thefreelibrary.com/_/print/PrintArticle.aspx?id=82059345.
Proudnikov, D. et al., "Chemical methods of DNA and RNA fluorescent labeling," Nucleic Acids Res. (1996) 24(22):4535-4542.
Puskas, L.G. et al., "Diamino-Antraquinone: A New Intercalating Agent. Synthesis and Linking to Oligodeoxynucleotide," *Nucleosides & Nucleotides* (1995) 14(3-5):967-968.
Rose, S.D. et al., "The Role of PTF1-P48 in pancreatic acinar gene expression," *J. Biol. Chem.* (2001) 276(47):44018-44026.

(56) References Cited

OTHER PUBLICATIONS

Schuster, G.B., "Long-range charge transfer in DNA: transient structural distortions control the distance dependence," Acc. Chem. Res. (2000) 33:253-260.
Setlow, P. et al., "Deoxyribonucleic acid polymerase: two distinct enzymes in one polypeptide," J. Biol. Chem. (1972) 247(1):224-231.
Sijm, D.T.H.M. et al., "Aqueous solubility, octanol solubility, and octanol/water partition coefficient of nine hydrophobic dyes," Envir. Toxic. Chem. (1999) 18(6):1109-1117.
Telser, J. et al., "Synthesis and characterization of DNA oligomers and duplexes containing covalently attached molecular labels: comparison of biotin, fluorescein, and pyrene labels by thermodynamic and optical spectroscopic measurements," J. Am. Chem. Soc. (1989) 111:6966-6967.
Tu, C-P.D. et al., "3'-end labeling of DNA with [α-32P]cordycepin-5'-triphosphate," Gene (1980) 10:177-183.
Zielske, A.G., "(Tosyloxy)anthraquinones: Versatile Synthons for the Preparation of Various Aminoanthraquinones," *J. Org. Chem.* (1987) 52:1305-1309.
International Preliminary Report on Patentability for Application No. PCT/US04/37932 dated Nov. 16, 2006 (8 pages).
International Search Report and Written Opinion for Application No. PCT/US04/37932 dated Jul. 28, 2006 (10 pages).
International Preliminary Report on Patentability for Application No. PCT/US03/029324 dated May 28, 2004 (4 pages).
International Search Report for Application No. PCT/US03/029324 dated Feb. 6, 2004 (1 page).
International Search Report and Written Opinion for Application No. PCT/US06/19552 dated Dec. 27, 2006 (9 pages).
United States Office Action for U.S. Appl. No. 10/987,608 dated Mar. 28, 2008 (8 pages).
United States Office Action for U.S. Appl. No. 10/987,608 dated Oct. 5, 2007 (7 pages).
United States Patent Office Action for U.S. Appl. No. 12/252,721 dated Apr. 30, 2010 (10 pages).
United States Patent Office Action for U.S. Appl. No. 12/252,721 dated Oct. 15, 2010 (9 pages).
United States Patent Office Action for U.S. Appl. No. 12/252,721 dated Apr. 20, 2011 (7 pages).
United States Patent Office Notice of Allowance for U.S. Appl. No. 12/252,721 dated Aug. 24, 2011 (6 pages).
United States Patent Office Action for U.S. Appl. No. 13/298,479 dated Jan. 10, 2012 (7 pages).
United States Patent Office Action for U.S. Appl. No. 13/298,479 dated Aug. 10, 2012 (26 pages).
United States Patent Office Notice of Allowance for U.S. Appl. No. 13/298,479 dated Oct. 11, 2012 (5 pages).
United States Office Action for U.S. Appl. No. 10/666,998 dated Jan. 8, 2008 (14 pages).
United States Office Action for U.S. Appl. No. 10/666,998 dated Jul. 16, 2008 (9 pages).
United States Office Action for U.S. Appl. No. 10/666,998 dated Jan. 16, 2009 (18 pages).
United States Office Action for U.S. Appl. No. 10/666,998 dated Sep. 17, 2009 (10 pages).
United States Patent Notice of Allowance for U.S. Appl. No. 10/666,998 dated Jan. 25, 2010 (12 pages).
United States Patent Office Action for U.S. Appl. No. 10/666,998 dated Jul. 1, 2010 (8 pages).
United States Patent Office Action for U.S. Appl. No. 12/853,755 dated Jul. 1, 2011 (20 pages).
United States Patent Office Notice of Allowance for U.S. Appl. No. 12/853,755 dated Nov. 8, 2011 (5 pages).
United States Patent Office Action for U.S. Appl. No. 12/623,811 dated Feb. 17, 2010 (5 pages).
United States Patent Office Action for U.S. Appl. No. 12/853,741 dated Nov. 26, 2010 (5 pages).
United States Patent Office Notice of Allowance for U.S. Appl. No. 12/853,741 dated Jun. 16, 2011 (2 pages).
United States Patent Office Action for U.S. Appl. No. 13/224,571 dated Jan. 31, 2012 (8 pages).
United States Patent Office Notice of Allowance for U.S. Appl. No. 13/224,571 dated Jun. 5, 2012 (23 pages).

\* cited by examiner

FLUORESCENCE QUENCHING AZO DYES, THEIR METHODS OF PREPARATION AND USE

CROSS-REFERENCE TO RELATED APPLICATIONS

This application is a continuation of U.S. application Ser. No. 13/298,479 filed Nov. 17, 2011, which is a divisional of U.S. application Ser. No. 12/252,721 filed Oct. 16, 2008, now U.S. Pat. No. 8,084,588, which is a divisional of U.S. application Ser. No. 10/987,608 filed Nov. 12, 2004, now U.S. Pat. No. 7,439,341, which claims priority benefits to U.S. Provisional Application No. 60/520,077 filed Nov. 14, 2003. These applications are incorporated herein by reference in their entirety.

FIELD OF THE INVENTION

This invention pertains to compositions that are capable of quenching the fluorescence of fluorophores and to methods for making and using them. The invention also provides kits that contain at least one of the disclosed quencher compositions.

BACKGROUND OF THE INVENTION

Light quenching processes that rely on the interaction of two dyes as their spatial relationship changes can be used in convenient processes for detecting and/or identifying nucleotide sequences and other biological phenomena. In one such method the change in fluorescence of a fluorescent donor or quencher can be monitored as two oligonucleotides (one containing a donor and one containing a quencher) bind to each other through hybridization. The binding can be detected without intervening purification steps that separate unhybridized from hybridized oligonucleotides.

Another method for detecting hybridization using fluorophores and quenchers is to link fluorescent donors and quenchers to a single oligonucleotide such that there is a detectable difference in fluorescence when the oligonucleotide is unhybridized as compared to when it is hybridized to its complementary sequence. For example, a partially self-complementary oligonucleotide designed to form a hairpin can be labeled with a fluorescent donor at one end and a quencher at the other end. Intramolecular annealing into the hairpin form can bring the donor and quencher into sufficient proximity for fluorescent quenching to occur. Intermolecular annealing of such an oligonucleotide to a target sequence disrupts the hairpin, which increases the distance between the donor and quencher and results in an increase in the fluorescent signal of the donor.

However, oligonucleotides are not required to have hairpins for this later method to work efficiently. The fluorophore and quencher can be placed on an oligonucleotide such that when it is unhybridized and in a random coil conformation, the quencher is able to quench fluorescence from the fluorophore. Once the oligonucleotide hybridizes to a complementary nucleotide sequence it becomes more extended and the distance between the fluorophore and quencher is increased, resulting in increased fluorescence.

Oligonucleotides labeled in a similar manner can also be used to monitor the kinetics of PCR amplification. In one version of this method the oligonucleotides are designed to hybridize to the 3' side ("downstream") of an amplification primer so that the 5'-3' exonuclease activity of a polymerase digests the 5' end of the probe, cleaving off one of the dyes. The fluorescence intensity of the sample increases and can be monitored as the probe is digested during the course of amplification.

Similar oligonucleotide compositions find use in other molecular/cellular biology and diagnostic assays, such as in end-point PCR, in situ hybridizations, in vivo DNA and RNA species detection, single nucleotide polymorphism (SNPs) analysis, enzyme assays, and in vivo and in vitro whole cell assays.

Perhaps the most common mechanism of fluorescent quenching is known as FRET (fluorescent resonance energy transfer). For FRET to occur a fluorescent donor and a fluorescent quencher must be within a suitable distance for the quencher to absorb energy from the donor. In addition, there must be overlap between the emission spectrum of the fluorescent donor and the absorbance spectrum of the quencher. This requirement complicates the design of probes that utilize FRET because not all potential quencher/donor pairs can be used. For example, the quencher known as BHQ-1, which absorbs light in the wavelength range of about 520-550 nm, can quench the fluorescent light emitted from the fluorophore, fluorescein, which fluoresces maximally at about 520 nm. In contrast, the quencher BHQ-3, which absorbs light in the wavelength range of about 650-700 nm would be almost completely ineffective at quenching the fluorescence of fluorescein through FRET but would be quite effective at quenching the fluorescence of the fluorophore known as Cy5 which fluoresces at about 670 nm. In general, the number of quenchers known that are capable of quenching the fluorescence of any given fluorophore is quite limited. For example with fluorescein, only a limited number of suitable quenchers are known and they are quite expensive to purchase commercially. Because fluorescein is one of the most commonly used fluorophores, new quenchers that can quench fluorescent light in the 520 nm range of fluorescein are needed. Similarly, quenchers for other known fluorophores are also needed.

Ideally, new quenchers will not fluoresce so that background fluorescence is minimized. This will allow for an increased signal to noise ratio in the probes that contain them, resulting in more sensitive probes. In addition, the lack of a secondary fluorescence facilitates the use of additional fluorophores in multiplexed assay formats which utilize multiple distinct probes each containing a different fluorophore. If a quencher emitted light in a region, then additional probes could not bear fluorophores that emit light in that region.

New quenchers should also have physical properties that facilitate their purification and the purification of probes into which they are incorporated. They should also be chemically stable so that they can be incorporated into biological probes and used in assays without significant degradation. The quenchers should contain suitable reactive moieties to provide for their convenient incorporation into biologically relevant compounds such as lipids, nucleic acids, polypeptides, and more specifically antigens, steroids, vitamins, drugs, haptens, metabolites, toxins, environmental pollutants, amino acids, peptides, proteins, nucleotides, oligonucleotides, polynucleotides, carbohydrates, and the like. Lastly, the most useful compositions should be easily manufactured.

The invention provides nonfluorescing, fluorescence-quenching compositions, some of which have strong fluorescence quenching properties in the 520 nm range. Moreover, the quenchers of the present invention are chemically stable and can be easily manufactured and purified. The compositions can be incorporated into biologically relevant compounds and, in many cases, impart useful purification properties to these compounds. These and other advantages of the invention, as well as additional inventive features, will be apparent from the description of the invention provided herein.

BRIEF SUMMARY OF THE INVENTION

The invention provides a novel group of azo quencher compositions that are useful as quenchers of fluorescence and to methods for making and using them. The quenchers of this invention are termed dark quenchers because they release the energy they absorb from fluorophores without giving off light. The quenchers contain an azo bond which joins $R_7$ to a conjugated ring system. The quenchers have the general formula shown below in Formula 1.

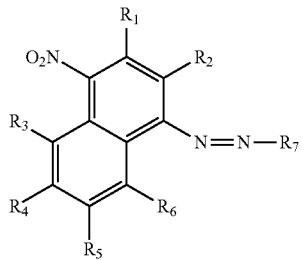

Formula 1

In Formula 1, $R_{1-6}$ can individually be electron withdrawing groups such as halogen, $NO_2$, $SO_3R$, $SO_2N(R)_2$, CN, NCS, keto, alkoxy groups, or $C_1$-$C_{10}$ alkyl groups, aryl groups, or heteroaryl groups. In addition, the $R_1/R_2$ pair, $R_3/R_4$ pair, $R_4/R_5$ pair and $R_5/R_6$ pairs can be combined to form ring structures having five or six ring members. These ring structures can be substituted. $R_7$ can be any aryl group that can be joined to the conjugated ring system by an azo bond to form a compound that is capable of quenching the fluorescence of a fluorophore. The quenchers can be derivatized to facilitate their conjugation to a variety of biologically relevant compounds, including lipids, nucleic acids, peptides, proteins, and the like. The invention also provides kits comprising, in one or more containers, at least one quencher dye composition of the present invention, and instructions for using that composition.

DETAILED DESCRIPTION OF THE INVENTION

Figure 1:
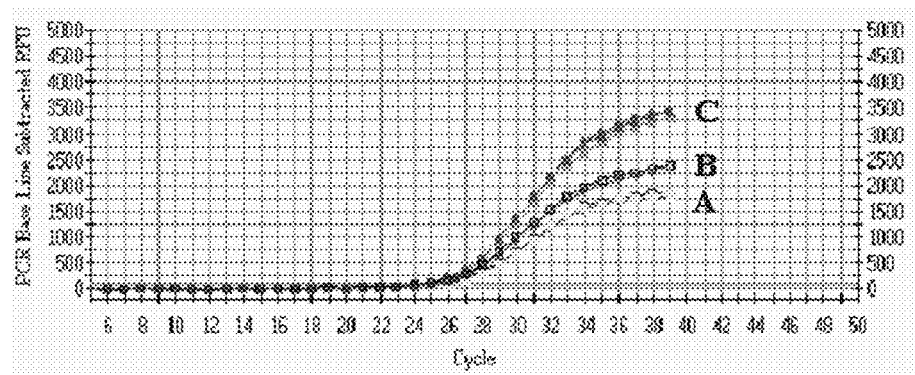
FIG. 1 shows the relative fluorescence collected during PCR reactions which contained three different probes (A-C). A is SEQ ID NO. 4 (AzoQuencher)-ACCCGTTCACCCTC-CCCCAGT-(6-FAM); B is for SEQ ID NO. 5 (6-FAM)-ACCCGTTCACCCTCCCCCAGT-(AzoQuencher); and C is for SEQ ID NO. 6 (6-FAM)-ACCCGTTCACCCTC-CCCCAGT-(BHQ2).

The invention provides a novel group of azo quencher compositions that are useful as quenchers of fluorescence and to methods for making and using them. The quenchers of this invention release the energy they absorb from fluorophores without giving off light. Consequently, they are called dark quenchers. The quenchers contain an azo bond and have the general formula shown below in Formula 1.

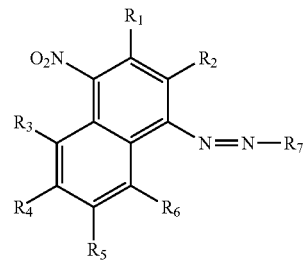

Formula 1

In Formula 1, $R_{1-6}$ can individually be electron withdrawing groups such as halogen, $NO_2$, $SO_3R$, $SO_2N(R)_2$, CN, NCS, keto, alkoxy groups, or $C_1$-$C_{10}$ alkyl groups, aryl groups, or heteroaryl groups. In addition, the $R_1/R_2$ pair, $R_3/R_4$ pair, $R_4/R_5$ pair and $R_5/R_6$ pairs can be combined to form ring structures having five or six ring members. These ring structures can be substituted. In certain embodiments one or more of $R_{1-6}$ can be hydrogen.

In Formula 1, $R_7$ can be any aryl group that can be joined to the conjugated ring system by an azo bond to form a compound that is capable of quenching the fluorescence of a fluorophore. Suitable aryl groups include phenyl, naphthyl, benzyl, xylyl, tolyl, pyridyl, and anilyl, among other groups. Preferably, the aryl groups are substituted or derivatized with at least one linking group for linking the quencher molecule to other molecules of interest.

In one preferred embodiment, $R_7$ is the compound of Formula 2, wherein the aryl ring is an aniline which can be substituted with various groups at positions L and L'.

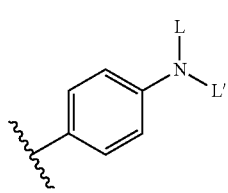

Formula 2

L and L' can be either nonreactive groups or reactive linking groups. For example, in one embodiment one of L or L' can be a nonreactive group such as an alkyl group, preferably an ethyl group, and the other can be a hydroxyethyl group which can be modified further to facilitate linking the quencher to other molecules of interest. Alternatively, both L and L' can be hydroxyethyl groups, as shown in Formula 3, below, either or both of which can be modified further for linking. One of skill in the art would recognize that hydroxy alkyl chains of any length or other linking groups, as described in more detail below, could be used to modify the aniline.

Formula 3

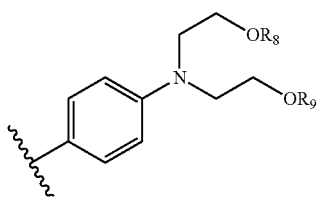

In Formula 3, the $R_8$ and $R_9$ groups can be any of a variety of linking groups which can be tailored for use. For example, one or both of $R_8$ and $R_9$ can be phosphoramidite groups such as diisopropylamino cyanoethyl phosphoramidite. Such a group would allow the quencher to react and become covalently attached to nucleophilic groups, particularly hydroxyl groups. In addition, one of $R_8$ or $R_9$ can be a hydroxyl protecting group such as a silyl group or a trityl group such as a mono, di, or tri-methoxytrityl group. More preferably, one of $R_8$ and $R_9$ is a trityl group and the other is a phosphoramidite group. In a preferred embodiment of Formula 1, the azo quencher composition has the structure of Formula 4 wherein one of $R_8$ or $R_9$ is a trityl group and the other is a phosphoramidite.

Formula 4

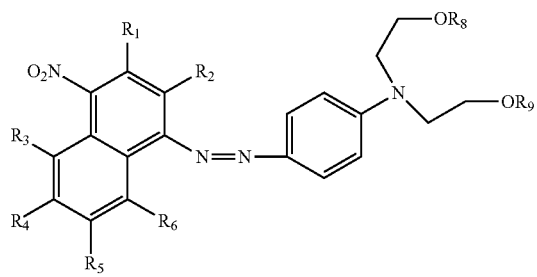

In one embodiment, the quencher is a compound of Formula 13:

Formula 13

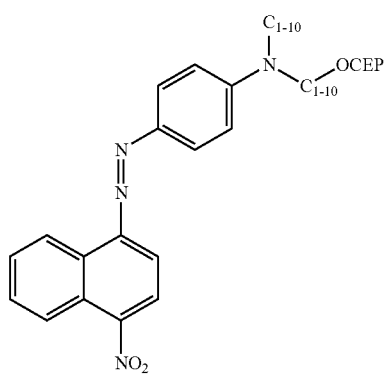

wherein CEP is cyanoethylphosphoramidite, and $C_{1-10}$ is a $C_1$ to $C_{10}$ alkyl group. In another embodiment, the quencher is a compound of Formula 14:

Formula 14

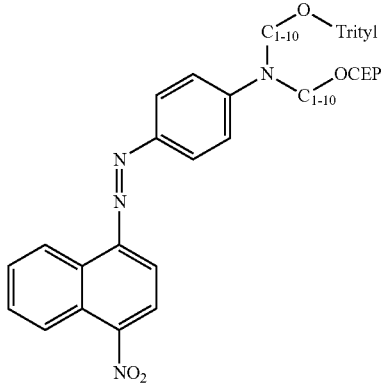

wherein trityl is an alkoxytrityl group, CEP is cyanoethylphosphoramidite, and $C_{1-10}$ is a $C_1$ to $C_{10}$ alkyl group.

The invention also contemplates methods for preparing the disclosed compositions. The reaction between the conjugated ring system and $R_7$ precursors can be carried out by treating a suitable conjugated ring precursor composition with a suitable nitrite, such as $NaNO_2$, or a suitable organic nitrite in a suitable solvent and subsequently with $LiBF_4$ to create a diazonium salt. The diazonium salt is then reacted with the $R_7$ precursor, an aryl composition, to generate an azo bonded ring system product. Methods for carrying out this reaction sequence are described in more detail in Examples 1 and 2.

Suitable conjugated ring precursor compounds have a primary amine and have the general structure of Formula 5. Specific embodiments of Formula 5 include the structures of Formulas 6-8.

Formula 5

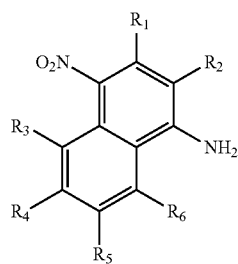

Formula 6

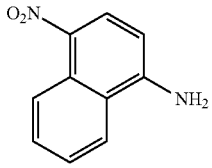

Formula 7

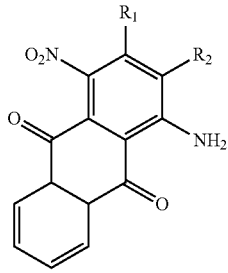

Formula 8

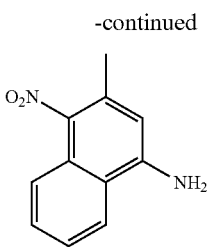

The azo quencher of Formula 1 can be further modified to facilitate its use. For example, reactive groups, such as amino, hydroxyl, and carboxyl groups on $R_5$ can be attached to linking groups or other molecules of interest. In one embodiment of Formula 4, $R_8$ can be reacted with a trityl group and $R_9$ can be reacted with N,N-diisopropylamino cyanoethyl phosphonamidic chloride, as described in Example 2, to generate a phosphoramidite reagent suitable for reaction with a variety of nucleophiles, especially including hydroxyl groups.

The phosphoramidite quenchers are ideally suited for incorporation into oligonucleotides. The phosphoramidite can be used to derivatize a solid support, as in Example 2, and the derivatized support can serve as the foundation for oligonucleotide synthesis by standard methods. Although Example 2 demonstrates the attachment of an azo-quencher compound to controlled pore glass, the method is more generally applicable to the attachment of the quencher to any solid support that contains a suitable number of free reactive nucleophilic groups, including polystyrene and polypropylene. The solid support-bound azo-quencher and trityl-protected, phosphoramidite quencher can both be used conveniently in conjunction with automated oligonucleotide synthesizers to directly incorporate the quencher into oligonucleotides during their chemical synthesis. In addition, the disclosed quenchers can be incorporated into oligonucleotides post synthetically. Such precursors and the oligonucleotides prepared with them are also contemplated by the present invention.

The disclosed quenching compositions can be linked to a variety of useful compounds other than oligonucleotides, provided that suitable reactive groups are present on those compounds. Such compounds include antigens, antibodies, steroids, vitamins, drugs, haptens, metabolites, toxins, environmental pollutants, amino acids, proteins, carbohydrates, lipids, and the like.

For purposes of this invention the term "linking group" refers to a chemical group that is capable of reacting with a "complementary functionality" of a reagent, e.g., to the hydroxyl group of a nucleic acid, and forming a linkage that connects the azo quenching compound of Formula 1 to the reagent. When the complementary functionality is an amine, preferred linking groups include such groups as isothiocyanate, sulfonylchloride, 4,6-dichlorotriazinyl, carboxylate, succinimidyl ester, other active carboxylate, e.g., —C(O) halogen, —C(O)OC$_{1-4}$ alkyl, or —C(O)OC(O)C$_{1-4}$ alkyl, amine, lower alkylcarboxy or —(CH$_2$)$_m$N$^+$(CH$_3$)$_2$(CH$_2$)$_m$ COOH, wherein m is an integer ranging from 2 to 12. When the complementary functionality is a hydroxyl group, the preferred linking group is a protected phosphoramidite. When the complementary functionality is sulfhydryl, the linking group can be a maleimide, halo acetyl, or iodoacetamide for example. See R. 35 Haugland (1992) Molecular Probes Handbook of Fluorescent Probes and Research Chemicals, Molecular Probes, Inc., disclosing numerous modes for conjugating a variety of dyes to a variety of compounds which sections are incorporated herein by reference.

The invention also is directed to nucleic acid compositions containing dye pairs, which include one of the disclosed quencher compositions and a fluorescent dye that fluorescences on exposure to light of the appropriate wavelength. Suitable fluorescent dyes in the dye pair are those that emit fluorescence that can be quenched by the quencher of the dye pair. In certain embodiments, the dye pair can be attached to a single compound, such as an oligonucleotide. In other embodiments, the fluorescent reporter dye and the quencher can be on different molecules.

A wide variety of reactive fluorescent reporter dyes are known in the literature and can be used so long as they are quenched by the corresponding quencher dye of the invention. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluoroscein, rhodamine or other like compound. Suitable fluorescent reporters include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16,17-octahydro-inner salt (TR or Texas Red); BODIPY™ dyes; benzoxaazoles; stilbenes; pyrenes; and the like. The fluorescent emission of certain reporter dyes is provided below.

| Fluorophore | Emission Max |
|---|---|
| 6-Carboxyfluorescein (6-FAM) | 520 nm |
| Tetrachlorofluorescein (TET) | 536 nm |
| Hexachlorofluorescein (HEX) | 556 nm |
| Cy3 | 570 nm |
| Tetramethylrhodamine (Tamra) | 580 nm |
| Cy3.5 | 596 nm |
| Carboxy-x-rhodamine (Rox) | 605 nm |
| Texas Red | 610 run |
| Cy5 | 667 nm |

-continued

| Fluorophore | Emission Max |
|---|---|
| Cy5.5 | 694 nm |

The quencher of Example 2 is capable of absorbing the fluorescent energy in the range of about 500 to about 620 nm and therefore can be used to quench the fluorescence of fluorescein through Texas Red.

Many suitable forms of these fluorescent reporter dyes are available and can be used depending on the circumstances. With xanthene compounds, substituents can be attached to xanthene rings for bonding with various reagents, such as for bonding to oligonucleotides. For fluorescein and rhodamine dyes, appropriate linking methodologies for attachment to oligonucleotides have also been described. See for example, Khanna et al. U.S. Pat. No. 4,439,356; Marshall (1975) Histochemical J., 7:299-303; Menchen et al., U.S. Pat. No. 5,188,934; Menchen et al., European Patent Application No. 87310256.0; and Bergot et al., International Application PCT/U590/05565).

Preferably, when the dye pair is in a configuration in which the reporter dye is effectively quenched by the quencher dye, its fluorescence is reduced by at least a factor of 80%, and more preferably by 90%, 95%, or 98%, when compared to its fluorescence in the absence of quenching. Compositions with 99%, 99.5%, 99.9% and higher levels of quenching have also been prepared with the quencher of Example 2. High levels of quenching allow for the preparation of oligonucleotide probes having a high signal to noise ratio which is defined as the amount of signal present when the composition is in its maximal unquenched state (signal) versus its maximally quenched state (noise).

Probes having a high signal to noise ratio are desirable for the development of highly sensitive assays. To measure signal to noise ratios relative fluorescence is measured in a configuration where the quencher and fluorophore are within the Förster distance and the fluorophore is maximally quenched (background fluorescence or "noise") and compared with the fluorescence measured when fluorophore and quencher are separated in the absence of quenching ("signal"). The signal to noise ratio of a dye pair of the invention will generally be at least about 2:1 but generally is higher. Signal to noise ratios of about 5:1, 10:1, 20:1, 40:1 and 50:1 are preferred. Ratios of 60:1, 70:1 and even up to 100:1 and higher can also be obtained in some cases. Intermediate signal to noise ratios are also contemplated.

Suitable dye-pairs can be used in many configurations. For example, the dye pair can be placed on nucleic acid oligomers and polymers. In this format, a dye-pair can be placed on an oligomer having a hairpin structure such that the fluorophore and quencher are within the Förster distance and FRET occurs.

In other embodiments, dye pairs can be placed on an oligomer that can adopt a random coil conformation, such that fluorescence is quenched until the oligonucleotide adopts an extended conformation, as when it becomes part of a duplex nucleic acid polymer. In general, the individual dye moieties can be placed at any position of the nucleic acid depending upon the requirements of use.

Nucleic acid oligomers and polymers that include the dye pairs of the invention can be used to detect target nucleic acids. In one method, the individual components of a dye-pair can be on opposing, annealable, self-complementary segments of a single oligonucleotide such that when the oligonucleotide anneals to itself in the absence of exogenous sequences, FRET occurs. The oligonucleotide is constructed in such a way that the internal annealing is disrupted and fluorescence can be observed when it hybridizes to nucleic acid polymers having sufficient complementarity. Such an oligonucleotide can be used to rapidly detect nucleic acid polymers having sequences that bind to the oligonucleotide. In another embodiment, such a composition comprises two biomolecules, such as oligonucleotides, one of which is attached to a reporter dye and the other of which is attached as a quencher dye.

Oligonucleotide probes lacking self-complementarity can also be utilized in a similar manner. For example, a quencher and fluorophore can be placed on an oligonucleotide that lacks the self-annealing property such that the random-coil conformation of the oligonucleotide keeps the fluorophore and quencher within a suitable distance for fluorescence quenching. Such oligonucleotides can be designed so that when they anneal to desired target nucleic acid polymers the fluorophore and quencher are more separated and the spectral characteristics of the fluorophore become more apparent.

Other DNA binding formats are also possible. For example, two oligonucleotides can be designed such that they can anneal adjacent to each other on a contiguous length of a nucleic acid polymer. The two probes can be designed such that when they are annealed to such a nucleic acid polymer a quencher on one of the oligonucleotides is within a sufficient proximity to a fluorophore on the other oligonucleotide for FRET to occur. Binding of the oligonucleotides to the nucleic acid polymer can be followed as a decrease in the fluorescence of the fluorophore.

Alternatively, a set of oligonucleotides that anneal to each other can be configured such that a quencher and a fluorophore are positioned within the Förster distance on opposing oligonucleotides. Incubation of such an oligonucleotide duplex with a nucleic acid polymer that competes for binding of one or both of the oligonucleotides would cause a net separation of the oligonucleotide duplex leading to an increase in the fluorescent signal of the reporter dye. To favor binding to the polymer strands, one of the oligonucleotides could be longer or mismatches could be incorporated within the oligonucleotide duplex.

These assay formats can easily be extended to multi-reporter systems that have mixtures of oligonucleotides in which each oligonucleotide has a fluorophore with a distinct spectrally resolvable emission spectrum. The binding of individual oligonucleotides can then be detected by determining the fluorescent wavelengths that are emitted from a sample. Such multi-reporter systems can be used to analyze multiple hybridization events in a single assay.

Oligonucleotides can also be configured with the disclosed quenchers such that they can be used to monitor the progress of PCR reactions without manipulating the PCR reaction mixture (i.e., in a closed tube format). The assay utilizes an oligonucleotide that is labeled with a fluorophore and a quencher in a configuration such that fluorescence is substantially quenched. The oligonucleotide is designed to have sufficient complementarity to a region of the amplified nucleic acid so that it will specifically hybridize to the amplified product. The hybridized oligonucleotide is degraded by the exonuclease activity of Taq polymerase in the subsequent round of DNA synthesis. The oligonucleotide is designed such that as the oligomer is degraded, one of the members of the dye-pair is released and fluorescence from the fluorophore can be observed. An increase in fluorescence intensity of the sample indicates the accumulation of amplified product.

Ribonucleic acid polymers can also be configured with fluorophores and quenchers and used to detect RNase. For example, a dye-pair can be positioned on opposite sides of an RNase cleavage site in an RNase substrate such that the fluorescence of the fluorophore is quenched. Suitable substrates include nucleic acid molecules that have a single-stranded region that can be cleaved and that have at least one internucleotide linkage immediately 3' to an adenosine residue, at least one internucleotide linkage immediately 3' to a cytosine residue, at least one internucleotide linkage immediately 3' to a guanosine residue and at least one internucleotide linkage next to a uridine residue and optionally can lack a deoxyribonuclease-cleavable internucleotide linkage. To conduct the assay, the substrate can be incubated with a test sample for a time sufficient for cleavage of the substrate by a ribonuclease enzyme, if present in the sample. The substrate can be a single-stranded nucleic acid molecule containing at least one ribonucleotide residue at an internal position. Upon cleavage of the internal ribonucleotide residue, the fluorescence of the reporter dye, whose emission was quenched by the quencher, becomes detectable. The appearance of fluorescence indicates that a ribonuclease cleavage event has occurred, and, therefore, the sample contains ribonuclease activity. This test can be adapted to quantitate the level of ribonuclease activity by incubating the substrate with control samples containing known amounts of ribonuclease, measuring the signal that is obtained after a suitable length of time, and comparing the signals with the signal obtained in the test sample.

Generally, any of the described assays could be conducted with positive controls to indicate proper function of the assay.

The invention also provides kits that include in one or more containers, at least one of the disclosed quenching dye compositions and instructions for its use. Such kits can be useful for practicing the described methods or to provide materials for synthesis of the compositions as described. Additional components can be included in the kit depending on the needs of a particular method. For example, where the kit is directed to measuring the progress of PCR reactions, it can include a DNA polymerase. Where a kit is intended for the practice of the RNase detection assays, RNase-free water could be included. Kits can also contain negative and/or positive controls and buffers.

The following examples further illustrate the invention but, of course, should not be construed as in any way limiting its scope. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus on the left to the 3'-terminus on the right.

Example 1

This example demonstrates the chemical synthesis of the compound of Formula 9. The abbreviation "CEP" in the formula stands for cyanoethylphosphoramidite.

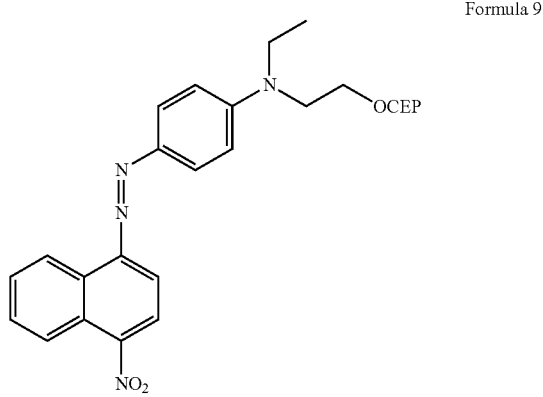

Formula 9

The synthesis was as shown in Scheme 1 below. Cold concentrated HCl (4.25 mL) was added to a suspension of 4-nitro-1-naphthylamine (0.5 g, 2.66 mmol) in water (1.6 mL) at 0° C. A solution of $NaNO_2$ (0.4 g) in water (1 mL) was added dropwise at 0° C. over 15 min and the 4-nitro-1-naphthylamine dissolved upon stirring. The solution was allowed to react for 10 min and then urea (0.16 g) was slowly added. Next, a solution of N-ethyl-N-hydroxyethyl-aniline (0.45 g) in acetic acid (2.18 mL) was mixed into the solution. After 15 mins, sodium acetate (5.31 g) in water (13.3 mL) was added slowly. The reaction mixture was stirred for 1 h at room temperature and the aqueous layer was then extracted twice with ethyl acetate. The organic layer was dried over $Na_2SO_4$ and subjected to flash chromatography with ethylacetate to give the azo alcohol (2) as a dark oil (0.5 g, 52% yield). MS (FAB+) [M+]: calc'd for $C_{20}H_{20}N_4O_3$, m/z 364.4; observed, m/z 365.

N,N-diisopropylamino cyanoethyl phosphonamidic chloride (0.46 mL, 2.06 mmol) was added dropwise at 0° C. to a solution of the azo alcohol (2) (0.5 g, 1.37 mmol) and triethylamine (0.38 mL, 2.74 mmol) in THF (20 mL). The mixture was stirred at room temperature for 2 h. $CH_2Cl_2$ was poured into the reaction mixtures and the organic layer washed twice with water and dried over $Na_2SO_4$. Flash chromatography on silica with the solvent EtOAc/PE/TEA: 20/70/10-40/50/10 gave 1 g of a dark oil representing nearly quantitative recovery. Analysis of the product by silica thin layer chromatography gave a product having an Rf of 0.49 in EtOAc/PE/TEA:40/50/10. MS (FAB+) [M+]: calc'd for $C_{29}H_{37}N_6O_4P$, m/z 564.2; observed, m/z 565.

The resulting phosphoramidite compound was used to prepare oligonucleotides containing the quencher moiety attached to the 5'-terminal hydroxyl group. The phosphoramidite quencher was added to the oligonucleotide during synthesis in the last addition reaction using standard automated phosphoramidate chemistry. Subsequently, the oligonucleotides were cleaved from the support, deprotected and purified using standard methods.

Scheme 1

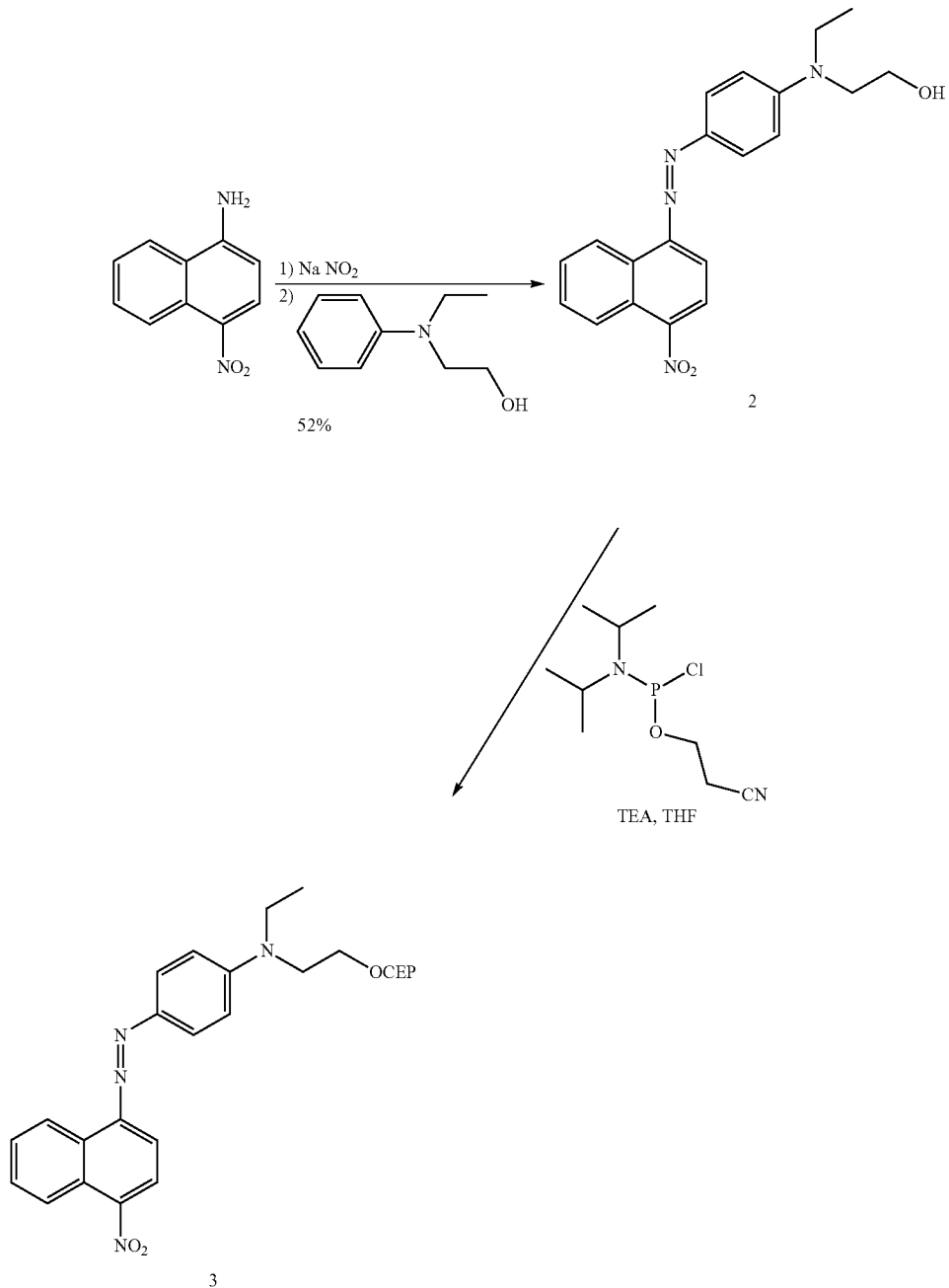

Example 2

This example demonstrates the synthesis of a controlled pore glass (CPG) support for oligonucleotide synthesis that is derivatized with a quencher of the present invention. The synthetic method is shown below in Schemes 2 and 3.

Mono-DMT-Phenyl Diethanolamine:

A solution of 10 g of phenyl diethanolamine in 100 mL of pyridine was mixed for 3-4 h at room temperature with a solution of 6 g dimethoxytrityl-chloride (DMT-Cl) in 150 mL of a 98:2 dichloromethane/pyridine solution. The reaction mixture was concentrated to dryness under vacuum. The residue was dissolved in 200 mL of ethyl acetate, washed with two portions of 100 mL of deionized water, and the organic layer dried over $Na_2SO_4$. The organic solution was concentrated and purified by column chromatography using a 300 g of silica gel column developed with 30/65/5 ethyl acetate/hexanes/triethylamine to yield 5.25 g (20% yield) of mono-DMT-phenyl diethanolamine. TLC: $R_f$ 0.55 (EtAc/hexanes/$Et_3$N-40/55/5). $^1$H NMR (CDCl$_3$) δ 7.38 (d, J=8 Hz, 2H), 7.27 (d, J=8 Hz, 4H), 7.38 (d, J=8 Hz, 2H), 7.24-7.12 (m, 6H), 6.76 (d, J=8 Hz, 4H), 6.66 (d, J=8 Hz, 2H), 3.74 (s, 6H), 3.74 (t, J=7.5 Hz, 2H), 3.54 (t, J=7.5 Hz, 2H), 3.51 (t, J=7.5 Hz, 2H), 3.33 (t, J=7.5 Hz, 2H), 2.23 (br. s, 1H).

Scheme 2

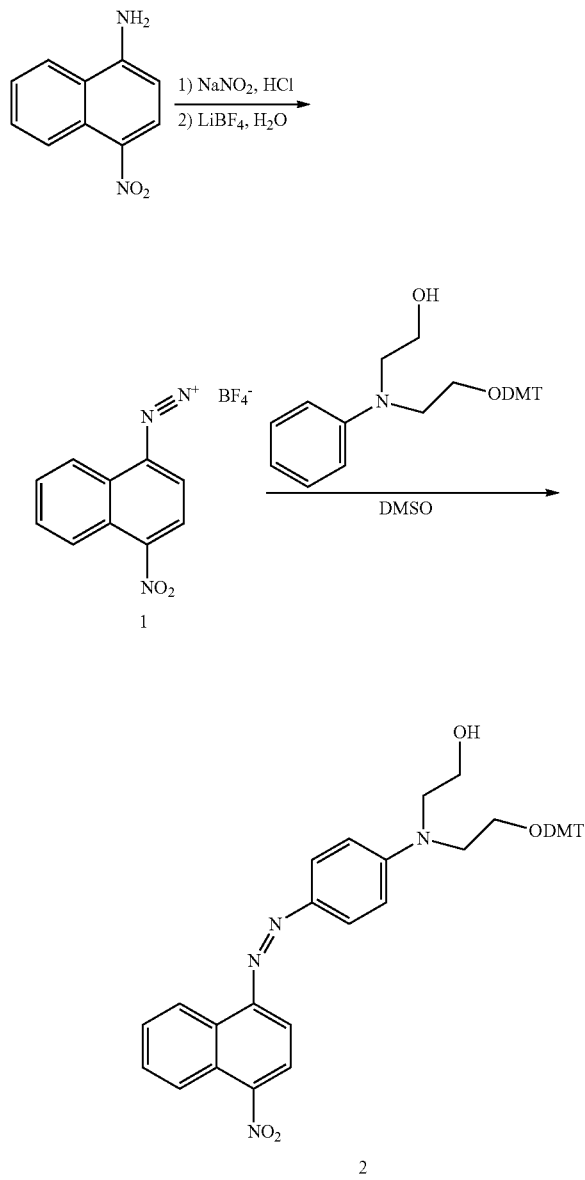

Mono-DMT-4-(1-nitro-4-naphthylazo)-N,N-diethanolaniline (2):

Cold concentrated HCl (17 mL) was added dropwise at 0° C. over 15 min to a suspension of 4-nitro-1-naphthylamine (2 g) in cold water (6 mL) at 0° C. Then NaNO$_2$ (1.6 g) in cold water (4 mL) was added dropwise at 0° C. over 15 min and the 4-nitro-1-naphthylamine dissolved upon stirring. LiBF$_4$ (1.38 g) in H$_2$O (3 mL) was added dropwise at 0° C. The reaction mixture was stirred at 0° C. for 30 min. A brownish yellow powder (3.08 g) of naphthyl-1-nitro-4-tetrafluoroborate diazonium salt (1) was obtained after filtering and rinsing the solution with cold water, methanol, and ether. A solution of 4 g of mono-DMT-phenyl diethanolamine in 50 mL of dimethylsulfoxide (DMSO) was added with stirring at 10-15° C. over 10-15 min to a chilled solution of 2.8 g of diazonium salt (1) in 50 mL of DMSO at 10-15° C. in a water bath. After an additional 15 min of stirring, 3 mL of triethylamine was added to the reaction mixture followed by 100 mL of ethyl acetate. The reaction mixture was washed with 3×30 mL of deionized water and the organic layer was dried over Na$_2$SO$_4$. The solvent was removed and product was purified by column chromatography with 300 g of silica gel to provide 1.8 g of mono-DMT-4-(1-nitro-4-naphthylazo)-N,N-diethanolaniline (2). TLC: R$_f$ 0.65 (DCM/Et$_3$N-80/20). $^1$H NMR (CDCl$_3$) δ 9.04 (d, J=8.4 Hz, 1H), 8.68 (d, J=8.4 Hz, 1H), 8.34 (d, J=8.4 Hz, 1H), 7.96 (d, J=9.2 Hz, 2H), 7.81-7.71 (m, 3H), 7.39 (d, J=8 Hz, 2H), 7.27 (d, J=8 Hz, 4H), 7.24-7.19 (m, 3H), 6.78 (d, J=8 Hz, 4H), 6.77 (d, J=8 Hz, 2H), 3.88 (t, J=7.5 Hz, 2H), 3.75 (s, 6H), 3.78-368 (m, 4H), 3.47 (t, J=7.5 Hz, 2H), 1.57 (br. s, 1H).

Mono-DMT-4-(1-nitro-4-naphthylazo)-N,N-diethanolaniline Phosphoramidite (3):

A solution of 0.2 ml of N,N-diisopropylamino-cyanoethyl-phosphoramidochloride was stirred into a solution of 0.3 g of alcohol (2) in 20 mL of anhydrous THF and 1 mL of triethylamine for 5 min at 0-5° C. After 15 min of additional stirring the reaction mixture was warmed to room temperature. The solvent was evaporated under a vacuum and the residue purified by column chromatography through 50 g of silica gel (EtOAc/PE/TEA:10/85/5-40/55/5). TLC: R$_f$ 0.65 (EtOAc/PE/Et$_3$N-40/55/5). $^1$H NMR (CDCl$_3$) δ 9.05 (d, J=8.4 Hz, 1H), 8.68 (d, J=8.4 Hz, 1H), 8.34 (d, J=8.4 Hz, 1H), 7.96 (d, J=9.2 Hz, 2H), 7.81-7.71 (m, 3H), 7.39 (d, J=8 Hz, 2H), 7.27 (d, J=8 Hz, 4H), 7.24-7.19 (m, 3H), 6.78 (d, J=8 Hz, 4H), 6.76 (d, J=8 Hz, 2H), 3.85-3.75 (m, J=7.5 Hz, 4H), 3.76 (s, 6H), 3.70 (t, J=7.5 Hz, 2H), 3.41 (t, J=7.5 Hz, 2H), 2.58 (t, J=8.0 Hz, 2H), 1.20 (s, 3H), 1.18 (s, 3H), 1.17 (s, 3H), 1.15 (s, 3H). $^{31}$P NMR δ 148.39.

Mono-DMT-4-(1-nitro-4-naphthylazo)-N,N-diethanolaniline-CPG 4:

One gram of 3'-phosphate CPG (see Formula 10), was treated with 3×10 mL of 3% (v/v) dichloroacetic acid in dichloromethane (DCM) and then washed with 5×10 ml of acetonitrile. A solution of 0.4 g of phosphoramidite (3) in 5 mL of dry acetonitrile and 5 mL of 0.45 M ethylthiotetrazole was added to CPG using an argon sparge. After 20 min the reaction mixture was removed, and the derivatized CPG was washed with 5×10 mL of acetonitrile. A 10 mL solution of 10% (v/v) acetic anhydride solution in THF and 10 mL of 10% (v/v) methylimidazole in 8:1 mixture of THF/pyridine were added to the resulting derivatized CPG using an Argon sparge. After 30 min the reaction mixture was removed and the derivatized CPG was washed with 5×10 mL of acetonitrile. A 10 mL solution of 0.02 M iodine in THF/pyridine/H$_2$O solution was added to the derivatized CPG for 5 min. Then the derivatized CPG was removed, and washed with 5×10 mL of acetonitrile and dried overnight in vacuum-desiccator to obtain 1.1 g of derivatized CPG (4).

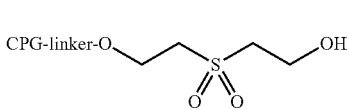

Formula 10

The derivatized support (4) was used to support oligonucleotide synthesis using standard oligonucleotide synthetic techniques. DMT group removal, nucleotide additions, and deprotection of the full length oligonucleotide were all carried out by standard methods. Oligonucleotides synthesized on this support had the quencher positioned at their 3'-terminal hydroxyl group.

Scheme 3
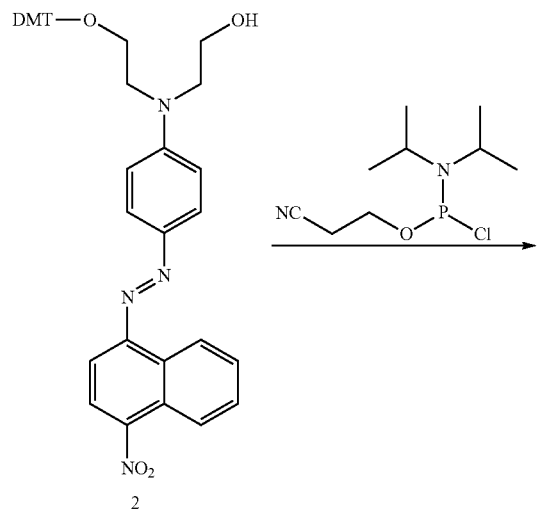
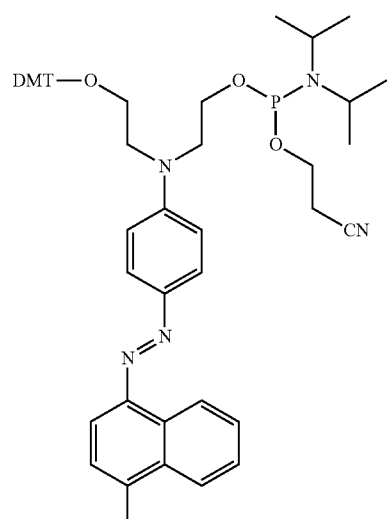
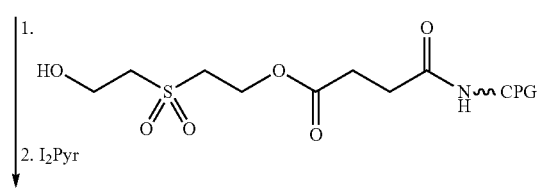

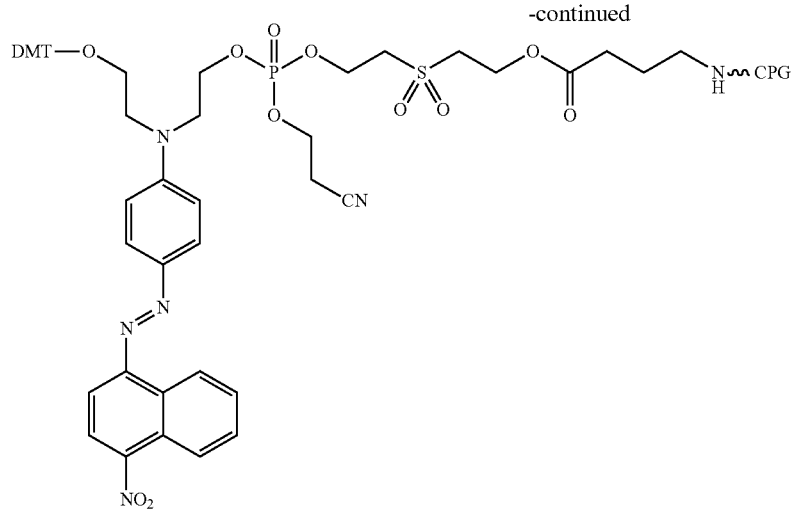

4

Example 3

This example demonstrates the signal to noise ratio (S:N) ratio of oligonucleotides containing both fluorescein and the azo quencher as prepared in Examples 1 and 2. The method involved measuring the relative fluorescence of the oligonucleotide while it was in a native single stranded configuration (background fluorescence or "noise") and comparing that with the fluorescence of the oligonucleotide measured when fluorophore and quencher are more separated ("signal"), as when the oligonucleotide is cleaved to separate the azo-quencher moiety from the fluorophore.

Oligonucleotide Synthesis.

Dual-labeled oligonucleotides were made with the azo-quencher at either the 5'-end or 3'-end of the molecule and with the fluorescein reporter group placed at the opposing end (6-FAM, single isomer 6-carboxyfluorescein, Glen Research, Sterling, Va.). For comparison, an oligonucleotide was made that incorporated a commercially available quenching group, the Black Hole Quencher™-2 group (Biosearch Technologies, Novato, Calif., hereinafter, BHQ_2). The oligonucleotides were purified by HPLC using standard methods. The oligonucleotides are shown below and are written with their 5'-termini to the left. The oligonucleotides were synthesized using standard automated phosphoramidite synthetic methods. For synthesis of SEQ ID No. 1, the Azo-Quencher prepared in Example 1 was added to the oligonucleotide in the last addition reaction as if it were another nucleotide addition. For synthesis of SEQ ID No. 2, the Azo-Quencher derivatized CPG described in Example 2 was used and nucleotides were added using standard automated methods.

| Probe | Sequence |
|---|---|
| SEQ ID No. 1 | (AzoQuencher)-ACCCGTTCACCCTCCC CCAGT-(6-FAM) |
| SEQ ID No. 2 | (6-FAM)-ACCCGTTCACCCTCCCCAG T-(AzoQuencher) |
| SEQ ID No. 3 | (6-FAM)-ACCCGTTCACCCTCCCCAG T-(BHQ_2) |

The structure of the oligonucleotide linkage to the 3'-Azo-Quencher group in oligonucleotide SEQ ID No. 2 is shown below in Formula 11. The linkage of the AzoQuencher to the oligonucleotide is through the 3'-hydroxyl group of the oligonucleotide.

Formula 11

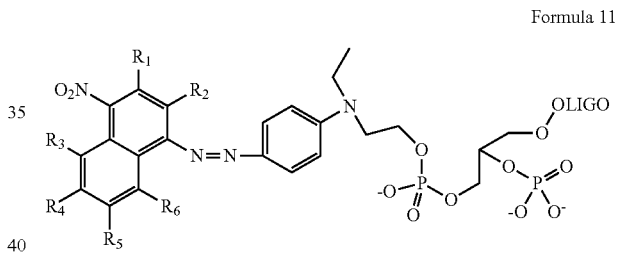

The structure of the oligonucleotide linkage to the 5'-Azo-Quencher group in oligonucleotide SEQ ID No. 1 is shown below in Formula 12. The linkage of the AzoQuencher to the oligonucleotide is through the 5'-hydroxyl group of the oligonucleotide.

Formula 12

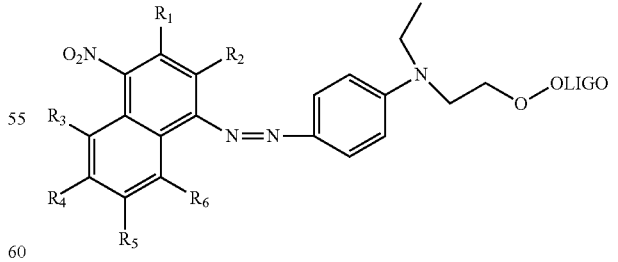

Signal to Noise (S:N) Assay of Fluorescence-Quenched Linear Probes.

Oligonucleotides were evaluated for 6-Fam quenching efficiency using the following protocol. Probe oligonucleotides (SEQ ID Nos. 1-3) were individually resuspended at 100 µM concentration in HPLC-grade water. From this stock solution, 2 mL of 100 nM probe solution was prepared with "STNR" Buffer, comprising 10 mM Tris pH 8.3, 50 mM KCl, 5 mM MgCl$_2$, 1 mM CaCl$_2$ which was split into two identical 1 mL fractions. One fraction was retained without enzyme treatment as the background control. The second fraction was subjected to nuclease degradation. Nuclease degradation was with micrococcal nuclease, 15 units (Roche, 15 U/μL) which was mixed into the oligonucleotide solution and incubated at 37° C. for 1 h. The relative fluorescence intensity of each sample was measured with a PTI QuantaMaster Model C-60 cuvette-based spectrofluorometer (Photon Technology International, Monmouth Jct., N.J.). The fluorescence of the solution containing undegraded (without nuclease enzyme treatment) probe was considered to be "background" or "noise." The fluorescence measurement of the solution containing degraded probe (with nuclease treatment) was treated as "signal."

The signal to noise ratios (S:N) were calculated and are shown below in Table 1.

TABLE 1

| Probe ID | Dye/Quencher 5'-3' | RFU Background | RFU Signal | S:N Ratio |
|---|---|---|---|---|
| SEQ ID No. 1 | AzoQuencher-6FAM | 4.20E+05 | 6.76E+06 | 16 |
| SEQ ID No. 2 | 6FAM-AzoQuencher | 7.36E+04 | 2.32E+06 | 31 |
| SEQ ID No. 3 | 6FAM-BHQ2 | 2.14E+05 | 5.43E+06 | 25 |

RFU = relative fluorescence units

As shown in Table 1 the signal to noise ratios (S:N Ratio) of SEQ ID Nos. 1-3 are all substantial and comparable, demonstrating that the novel azo-quencher of this invention is capable of quenching a fluorescein with similar or better efficiency than a commonly employed commercially available quencher group. The azo-quencher will also be effective at quenching a variety of other fluorescent reporter dyes, including tetrachlorofluorescein, hexachlorofluorescein and Texas Red.

Example 4

Fluorescence-quenched probes are frequently used to detect target nucleic acid sequences using amplification reactions, such as the polymerase chain reaction (PCR) (Mullis et. al., 1986). This example demonstrates the use of fluorescent probes that contain the Azo-Quencher of this invention to detect PCR amplified DNA.

Oligonucleotide primers and probes were synthesized as described in Example 3. Primers, probes, and target nucleic acids were as shown in Table 2 below. Probes used were SEQ ID No. 4-6. Primers used are SEQ ID No. 7 and 8. The target nucleic acid is SEQ ID No. 9, a 220 basepair (bp) amplicon derived from the murine bHLH protein Ptfl-p48 gene (Genbank #AF298116), cloned into the pCRII-TOPO vector (Invitrogen, Carlsbad, Calif.), and is hereafter referred to as the "p48-gene target".

TABLE 2

| Probes: | |
|---|---|
| SEQ ID No. 4 | (AzoQuencher)-ACCCGTTCACCCTCCCCCAGT-(6-FAM) |
| SEQ ID No. 5 | (6-FAM)-ACCCGTTCACCCTCCCCCAGT-(AzoQuencher) |
| SEQ ID No. 6 | (6-FAM)-ACCCGTTCACCCTCCCCCAGT-(BHQ2) |
| Forward Primer: MP48 F968 | |
| SEQ ID No. 7 | CAGAAGGTTATATCTGCCATCG |
| Reverse Primer: MP48 R1187 | |
| SEQ ID No. 8 | CTCAAAGGGTGGTTCGTTCTCT |
| Target Nucleic Acid Sequence | |
| SEQ ID No. 9 | Forward Primer                   Probe<br>CAGAAGGTTATCATCTGCCATCGAGGCACCCGTTCACCCTCCCCCAGTGA<br>CCCGGATTATGGTCTCCCTCCTCTTGCAGGGCACTCTCTTTCCTGGACTGA<br>TGAAAAACAGCTCAAAGAACAAAATATCATCCGTACAGCTAAAGTGTGG<br>ACCCCAGAGGACCCCAGAAAACTCAACAGTCAAATCTTTCGACAACATA<br>GAGAACGAACCACCCTTTGAG<br>                    Reverse Primer |

PCR amplification was done with the Stratagene (La Jolla, Calif.) Brilliant Plus™ Quantitative PCR core Reagent Kit according to the manufacturer's directions. Reactions were carried out in a 25 μL volume with 200 nM each of the amplification primers and fluorescent quenched probe and 5000 copies of target DNA. Cycling conditions were 50° C. for 2 min, 95° C. for 10 min, then 40 cycles of 2-step PCR with 95° C. for 15 sec and 60° C. for 1 min. An ABI Prism™ 7000 Sequence Detector (Applied Biosystems Inc., Foster City, Calif.) was used for PCR and fluorescence measurements. All assays were performed in triplicate. Results for different probes are presented in Table 3 below. In Table 3, the cycle threshold (Ct) value is defined as the cycle at which a statistically significant increase in fluorescence is detected above background. A lower Ct value is indicative of a higher concentration of target DNA. Table 3 shows that assays with each oligonucleotide probe had similar Ct values and therefore functioned similarly in these assays.

TABLE 3

| Probes: | Sequence | Ave. Ct |
|---|---|---|
| SEQ ID No. 4 | (AzoQuencher)-ACCCGTTCACCCTCCC CCAGT-(6-FAM) | 24.3 |
| SEQ ID No. 5 | (6-FAM)-ACCCGTTCACCCTCCCCCAG T-(AzoQuencher) | 23.6 |

TABLE 3-continued

| SEQ ID No. 6 | (6-FAM)-ACCCGTTCACCCTCCCCCAG T-(BHQ2) | 23.2 |

Relative fluorescence levels collected during PCR for each probe were graphically plotted against cycle number and are shown in FIG. 1. This example demonstrates that probe compositions comprising the new azo-quenchers of the invention perform well in a quantitative real-time PCR assay and are functionally equivalent to probes that contain other quencher moieties.

Example 5

This example shows an absorbance spectrum of an oligonucleotide modified at its 5' terminus to contain the AzoQuencher of Formula 8 in Example 1. The oligonucleotide was made using standard automated phosphoramidite nucleotide synthetic methods where the last addition cycle was carried out with the molecule of Formula 8. The composition of the oligonucleotide is shown below.

SEQ ID No. 10
(Azo-Quencher)-CAGAGTACCTGA

Once synthesized, the oligonucleotide was suspended in HPLC-grade water at 400 nM concentration. Optical absorbance was measured in 10 mM Tris pH 8.0, 1 mM EDTA (TE buffer) with a sub-micro quartz cuvette with 1-cm path length in a Hewlett Packard Model 8453 spectrophotometer (Hewlett Packard, Palo Alto, Calif.). Absorbance density was recorded from 220 nm to 700 nm and is shown in FIG. 2.

Figure 2:
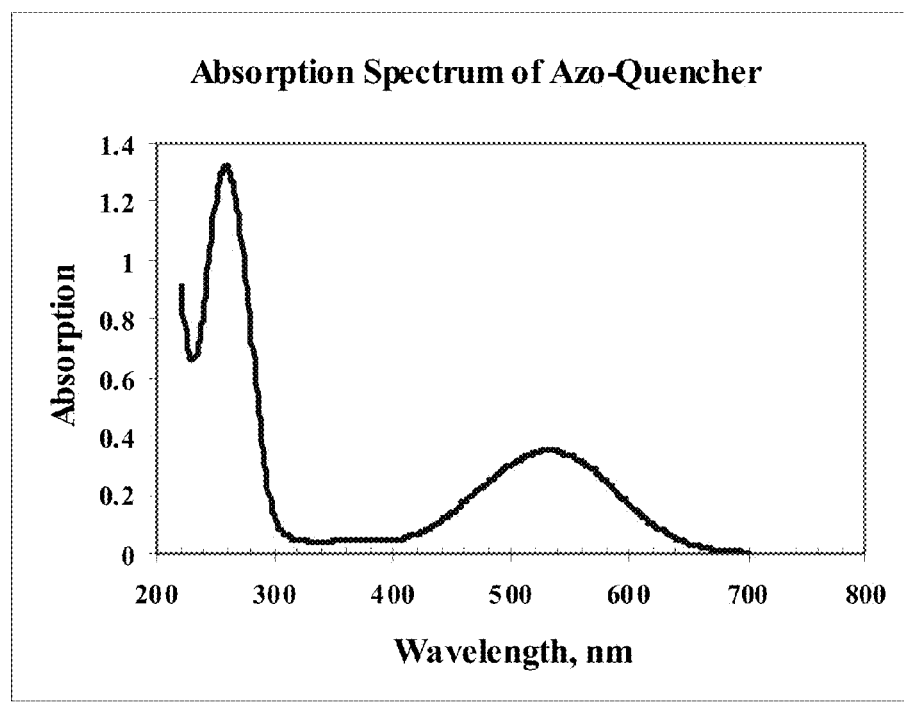
FIG. 2 shows the absorbance spectrum of an oligonucleotide SEQ ID NO. 10 having the composition (AzoQuencher)-CAGAGTACCTGA

As shown in FIG. 2, the absorbance spectrum is broad, ranging from 420 to 620 nm, with peak absorbance at 531 nm. This absorbance range overlaps with the fluorescence emission of a wide variety of fluorophores commonly used in molecular biology applications. For FRET based quenching mechanisms, this spectrum is positioned to offer maximum quenching capacity for dyes in the spectral range of fluorescein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for making an oligonucleotide, comprising introducing the compound of Formula 1 to an automated oligonucleotide synthesizer to chemically incorporate a quencher compound into the oligonucleotide:

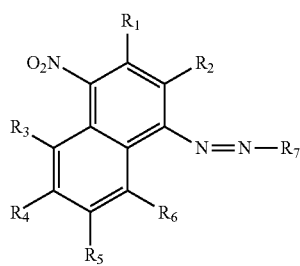

Formula 1 wherein $R_{1-6}$ on the conjugated ring system are individually an electron withdrawing group, alkyl group, aryl group, hydrogen, heteroaryl group, or a five or six member ring structure formed from the $R_1$, $R_2$ pair, the $R_3$, $R_4$ pair, the $R_4$, $R_5$ pair, or the $R_5$, $R_6$ pair; and wherein $R_7$ is an anilyl group of Formula 2:

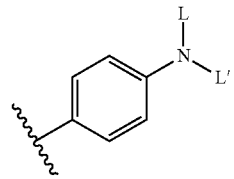

Formula 2 wherein L and L' are the same or different and are a $C_{1-10}$ group, $-C_{1-10}-O-R_8$, or $-C_{1-10}-O-R_9$, wherein $C_{1-10}$ is a $C_{1-10}$ alkyl group, and $R_8$ and $R_9$ are independently a hydrogen, trityl, alkoxytrityl, silyl, or phosphoramidite with the proviso that when L or L' is ethyl, then the other is not hydroxyethyl, and wherein at least one of L or L' is $-C_{1-10}-O-R_8$ or $-C_{1-10}-O-R_9$, and at least one of $R_8$ and $R_9$ is a phosphoramidite.

2. The method of claim 1, wherein the phosphoramidite group is a cyanoethylphosphoramidite.

3. The method of claim 2, wherein the quencher compound is coupled to the 3'-terminus of the oligonucleotide.

4. The method of claim 3, wherein the quencher compound is coupled to the 5'-terminus of the oligonucleotide.

5. The method of claim 1, wherein the synthesis step comprises linking the compound of Formula 1 to a solid support.

6. The method of claim 5, wherein the solid support is controlled pore glass.

7. The method of claim 1, wherein the compound of Formula 1 is the compound of Formula 13:

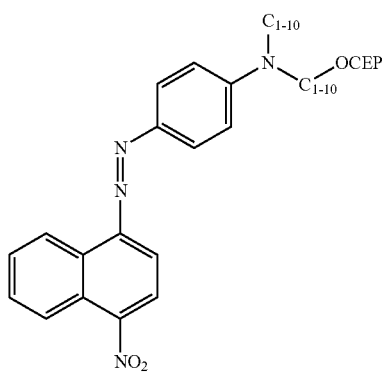

Formula 13 wherein CEP is cyanoethylphosphoramidite.

8. The method of claim 1, wherein the compound of Formula 1 is the compound of Formula 14:
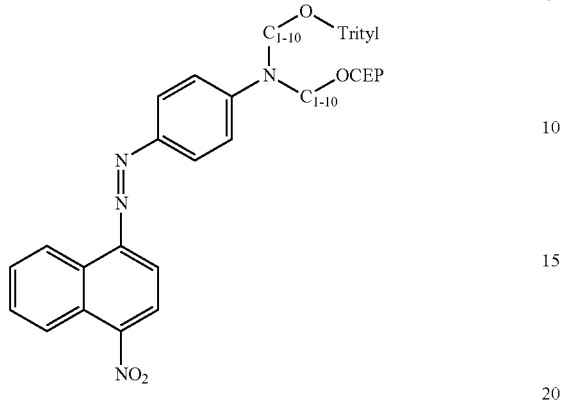
Formula 14
wherein CEP is cyanoethylphosphoramidite.
9. The method of claim 1, wherein the oligonucleotide further comprises a fluorophore.
* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1
acccgttcac cctcccccag t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
acccgttcac cctcccccag t                                              21
```

```
<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
acccgttcac cctcccccag t                                                   21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
acccgttcac cctcccccag t                                                   21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
acccgttcac cctcccccag t                                                   21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
acccgttcac cctcccccag t                                                   21

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
cagaaggtta tatctgccat cg                                                  22

<210> SEQ ID NO 8
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 8
ctcaaagggt ggttcgttct ct                                                  22

<210> SEQ ID NO 9
<211> LENGTH: 220
<212> TYPE: DNA
<213> ORGANISM: Artificial Sequence
<220> FEATURE:
```

```
<223> OTHER INFORMATION: Synthetic oligonucleotide

<400> SEQUENCE: 9
cagaaggtta tcatctgcca tcgaggcacc cgttcaccct ccccagtga cccggattat      60 ggtctccctc ctcttgcagg gcactctctt tcctggactg atgaaaaaca gctcaaagaa    120
caaaatatca tccgtacagc taaagtgtgg accccagagg accccagaaa actcaacagt    180
caaatctttc gacaacatag agaacgaacc acccttttgag                         220

<210> SEQ ID NO 10
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 10
cagagtacct ga                                                         12
```